United States Patent
Tomich et al.

(10) Patent No.: US 10,961,547 B2
(45) Date of Patent: Mar. 30, 2021

(54) MULTIFUNCTIONAL METALLIC NANOPARTICLE-PEPTIDE BILAYER COMPLEXES

(71) Applicant: Kansas State University Research Foundation, Manhattan, KS (US)

(72) Inventors: John M. Tomich, Manhattan, KS (US); Pinakin R. Sukthankar, Lawrence, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 299 days.

(21) Appl. No.: 15/521,835

(22) PCT Filed: Nov. 4, 2015

(86) PCT No.: PCT/US2015/058937
§ 371 (c)(1),
(2) Date: Apr. 25, 2017

(87) PCT Pub. No.: WO2016/073548
PCT Pub. Date: May 12, 2016

(65) Prior Publication Data
US 2017/0232116 A1    Aug. 17, 2017

Related U.S. Application Data (60) Provisional application No. 62/075,455, filed on Nov. 5, 2014.

(51) Int. Cl.
| | | |
|---|---|---|
| *A61K 38/08* | (2019.01) | |
| *A61K 38/28* | (2006.01) | |
| *C12N 15/88* | (2006.01) | |
| *C12N 15/87* | (2006.01) | |
| *A61K 47/64* | (2017.01) | |
| *A61K 47/69* | (2017.01) | |

(52) U.S. Cl.
CPC ........... *C12N 15/88* (2013.01); *A61K 38/08* (2013.01); *A61K 38/28* (2013.01); *A61K 47/645* (2017.08); *A61K 47/6923* (2017.08); *C12N 15/87* (2013.01)

(58) Field of Classification Search
None
See application file for complete search history.

(56) References Cited

U.S. PATENT DOCUMENTS

| | | | |
|---|---|---|---|
| 7,745,570 B2 | 6/2010 | Tomich et al. | |
| 8,883,967 B2 | 11/2014 | Tomich et al. | |
| 2011/0097275 A1* | 4/2011 | Arbogast | A61K 49/223 424/9.5 |
| 2012/0021020 A1* | 1/2012 | Tomich | A61K 9/1075 424/400 |
| 2013/0217037 A1* | 8/2013 | Brisson | G01N 33/54346 435/7.23 |
| 2013/0261013 A1* | 10/2013 | Baltzer | C12N 9/1211 506/9 |
| 2013/0261292 A1 | 10/2013 | Gang et al. | |
| 2014/0296551 A1 | 10/2014 | Sun et al. | |

FOREIGN PATENT DOCUMENTS

WO    2014/033263    3/2014

OTHER PUBLICATIONS

Di Marco et al. (Int J Nanonnedicine. 2010; 5: 37-49) (Year: 2010).*
International Search Report and Written Opinion dated Feb. 2, 2016, in PCT/US15/58937, filed Nov. 4, 2015.

* cited by examiner

Primary Examiner — Sergio Coffa
(74) Attorney, Agent, or Firm — Hovey Williams LLP (57) ABSTRACT

Described are nanoparticulates comprising a metallic nanoparticle core and a peptide coating or shell encapsulating the nanoparticle core and being covalently bonded thereto. The coating is formed from a plurality of branched, amphipathic peptides, each comprising a polar/positively charged C-terminal segment, a branch point, and two hydrophobic N-terminal segments extending from the branch point. Methods of forming and using the nanoparticulates are also described. When a plurality of first and second peptides are added sequentially to the nanoparticle core, the peptides they self-assemble to form an interlocking peptide network bilayer where the respective hydrophobic segments of the peptides form beta-sheet structures in which the opposed sequences interlock to form a zipper-like structure in three dimensions.

25 Claims, 5 Drawing Sheets

Specification includes a Sequence Listing.

MULTIFUNCTIONAL METALLIC NANOPARTICLE-PEPTIDE BILAYER COMPLEXES

CROSS-REFERENCE TO RELATED APPLICATIONS

The present application is the National Stage of International Patent Application No. PCT/US2015/058937, filed Nov. 4, 2015, which claims the priority benefit of U.S. Provisional Patent Application Ser. No. 62/075,455, filed Nov. 5, 2014, entitled MULTIFUNCTIONAL GOLD NANOPARTICLE-PEPTIDE BILAYER COMPLEXES, each of which is incorporated by reference in its entirety herein.

SEQUENCE LISTING

The following application contains a sequence listing in computer readable format (CRF), submitted as a text file in ASCII format entitled "SequenceListing," created on Nov. 2, 2015, as 2 KB. The content of the CRF is hereby incorporated by reference.

BACKGROUND OF THE INVENTION

Field of the Invention

The present invention relates to synthetic peptide-coated nanoparticles, and particularly peptide bilayer-coated nanoparticles.

Description of Related Art

Figure 1:
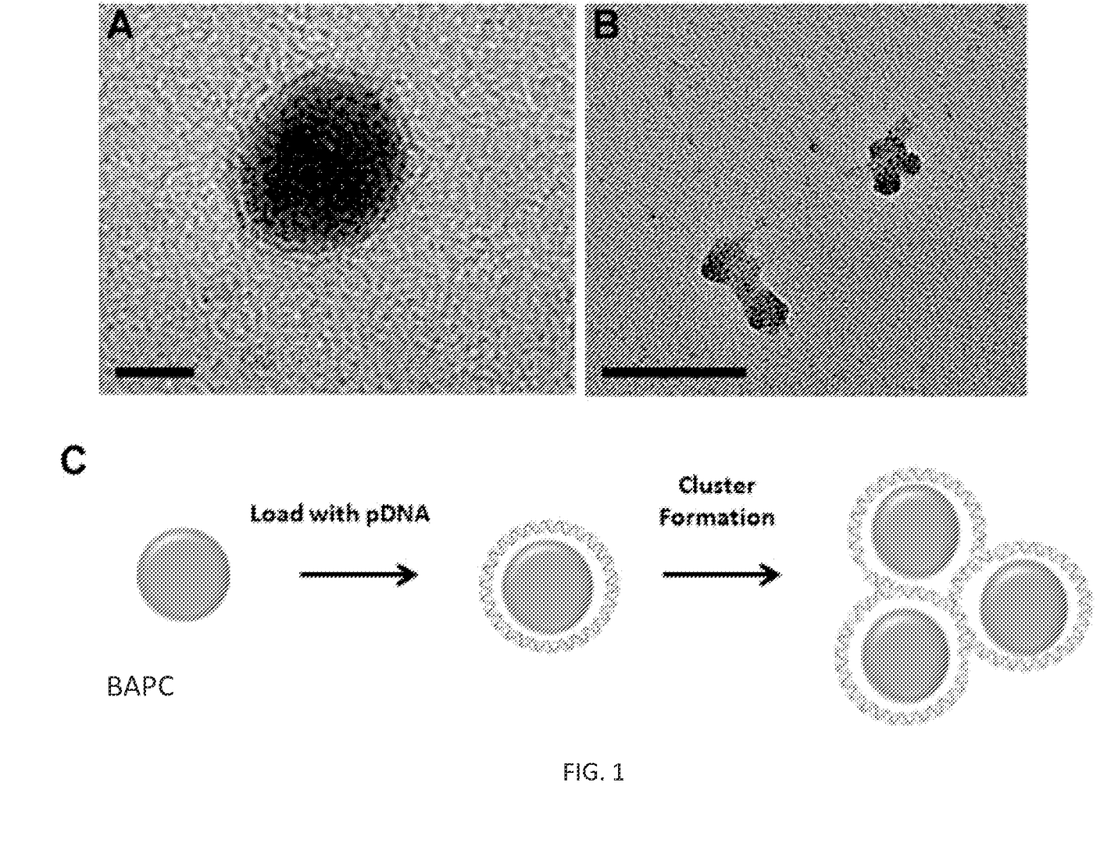
FIG. 1 shows: (A) Single BAPCs interacting with pDNA (Scale bar=5 nm). (B) Cluster of BAPCs interacting with DNA; and (C) Schematic illustration of the BAPCs-DNA interaction (Scale bar=100 nm)
Figure 2:
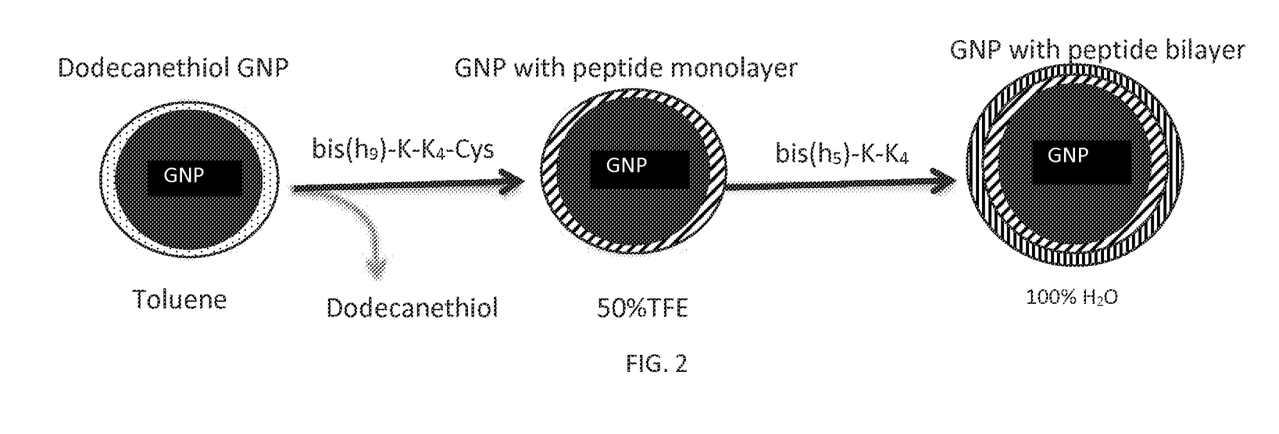
FIG. 2 is an illustration of coating the surface of 5 nm gold nanoparticle with a modifiable branched peptide bilayer.
Figure 3:
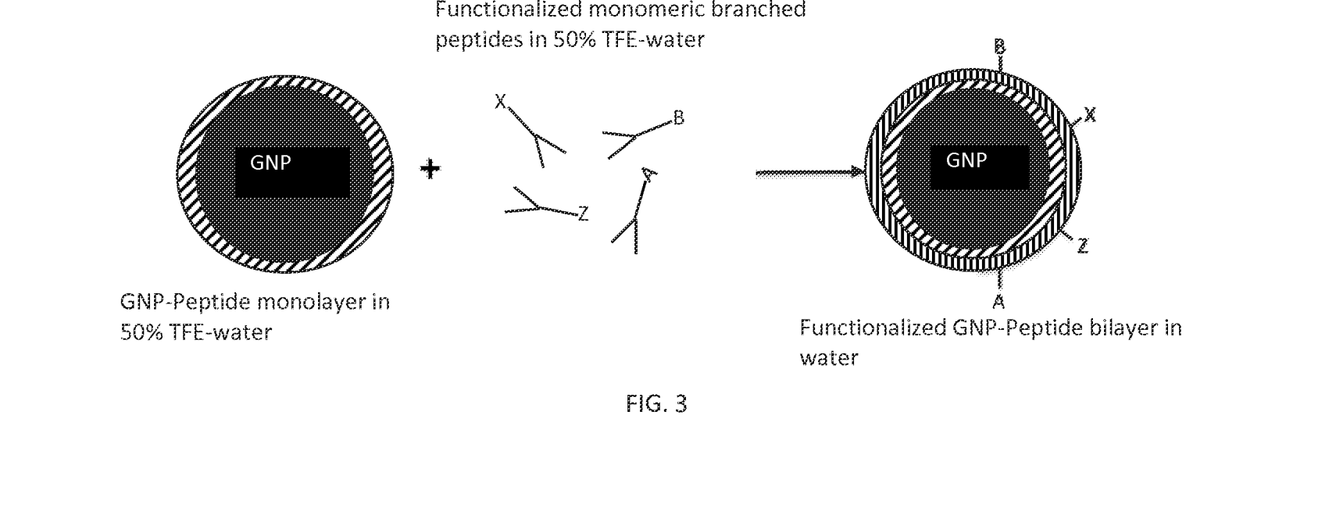
FIG. 3 is an illustration of the ability to produce multifunctionalized nanoparticles by pre-functionalizing the peptide sequences before adding to a monolayer-coated nanoparticle to create the self-assembled peptide bilayer with the functional moieties extending from the surface of the bilayer.

In previous studies we have demonstrated that branched amphiphilic peptides (BAPs)-spontaneously co-assemble at room temperature to form bilayer delimited poly-cationic capsules (BAPCs) or vesicles having a liquid-receiving hollow core. The BAPCs are readily taken up by cultured cells through the endocytic pathway, escape the late endosomes and ultimately accumulate in the perinuclear region, persisting there without apparent degradation. To date we have entrapped small proteins and solutes as well as stably encapsulated alpha particle emitting radionuclides within the BAPCs. The earlier work used 20-30 nm peptide bilayer delimited capsules (BAPCs) that can be coated with DNA. FIGS. 1(A)-(C) show TEM images and cartoon images of the BACP:DNA assemblies at N:P=20.8.

SUMMARY OF THE INVENTION

The present disclosure is broadly concerned with nanoparticulates. The nanoparticulates comprise a metallic nanoparticle core and a peptide coating encapsulating the nanoparticle core. The peptide coating is covalently bonded to the surface of the nanoparticle core. The peptide coating comprises a plurality of branched, amphipathic peptides. Each of these peptides comprises a C-terminal hydrophilic segment ("head") coupled to a branch point, where the branch point is coupled to two respective N-terminal hydrophobic segments ("tails").

Compositions comprising a plurality of nanoparticulates according to the various embodiments of the invention are also described herein. The nanoparticulates are dispersed in a pharmaceutically-acceptable carrier or excipient.

The present disclosure is also concerned with methods of targeting delivery of an active agent to a region of a patient. The methods comprise administering to a patient a plurality of nanoparticulates according to the various embodiments of the invention. The nanoparticulates each further comprises at least one functional moiety extending from the surface of the peptide coating to direct selective uptake and targeted delivery of the nanoparticulates to the desired region of the patient.

Methods of transfecting a cell are also described. The methods comprise incubating cells with a nanoparticulate according to the various embodiments of the invention. The nanoparticulate further comprises nucleic acid bound to the surface of the peptide coating.

DETAILED DESCRIPTION

In more detail, the present disclosure is concerned with multifunctional nanoparticulates and methods of making and using the same. The nanoparticulates each comprise (consist essentially or even consist of) a metallic nanoparticle core and a peptide coating or shell encapsulating the nanoparticle core, with optional functional groups attached to the coating. The nanoparticle core is preferably a solid core (as opposed to being hollow). More particularly, each nanoparticulate preferably comprises a single individual nanoparticle core encapsulated with a peptide coating. In one or more embodiments, the metallic nanoparticle core is gold nanoparticle, a silver nanoparticle, or a copper nanoparticle. Metallic nanoparticles can be particles of various shapes and sizes, where the term "nanoparticle" specifically refers herein to nanosized particles with maximum surface-to-surface dimensions of 100 nm or less. For example, in the case of a nanosphere, the maximum surface-to-surface dimension would be its diameter. Likewise, for a nanorod, the maximum surface-to-surface dimension would be the length as measured along its longest axis. In one or more embodiments, the maximum surface-to-surface dimension of the metallic nanoparticle core is from about 1 nm to about 100 nm, more preferably from about 1 nm to about 50 nm, even more preferably from about 1 nm to about 10 nm, and most preferably from about 1 to about 7 nm. The nanoparticle population used in preparing the nanoparticulates is preferably substantially monodisperse, with a very narrow size/mass size distribution. More preferably, the nanoparticle population has a polydispersity index of from about 1.2 to about 1.05. It is particularly preferred that the nanoparticles used in the inventive particulates are discrete particles. That is, clustering of nanocrystals (i.e., nanocrystalline particles) is preferably avoided.

As noted, the metallic nanoparticle core is coated with peptides. Preferably, the peptides can be attached directly to the outer surface of the nanoparticle. In one or more embodiments, the peptides are covalently bonded to the nanoparticle surface. In one or more embodiments, the peptides comprise head groups that have an added cysteine residue at the C-terminus of the peptide, wherein the head groups are attached through a covalent bond between the sulfur of the added cysteine to the nanoparticle surface. The outer surface of the nanoparticle surface will preferably be essentially completely covered with peptides. That is, at least about 70%, preferably at least about 90%, and more preferably about 100% of the surface of the nanoparticle will have attached peptides.

Unlike existing linear peptide diblock copolymers, the inventive copolymers used in forming the peptide coatings of the present invention preferably comprise (consist essentially or even consist of) branched/non-linear synthetic peptide sequences. The peptides can either be of the all L-stereo configuration or D-stereo configuration. The peptides are amphipathic and comprise an oligo-lysine (K=n) C-terminus with the alpha- and epsilon-amino groups of the N-terminal lysine acting as the branch points for two hydrophobic beta-sheet forming sequences. The resulting peptides, in their broadest terms, have a terminal hydrophilic (polar) segment, a branch point, and two terminal hydrophobic segments. Thus, the hydrophobic segments of the peptides are each preferably coupled to the same amino acid residue which serves as the branch point attached to the hydrophilic segment, resulting in a terminal hydrophilic "head" and two terminal hydrophobic "tails," similar to the morphology of a class of lipids called diacylphospholipids.

The hydrophilic (polar) lysine head group sequences are preferably from about 1 to about 7 lysine residues in length, more preferably from about 1 to about 6 lysine residues, and even more preferably from about 1 to about 5 lysine residues. A particularly preferred lysine sequence is KKKK (SEQ ID NO: 1). The lysines can have a net positive charge at physiological pH values (7.2-7.4). A further uncharged N-terminal lysine residue is provided in the peptide as the branch point (—K—). Alternative branch points that could be used instead of lysine (—K—) include diaminopropionic acid, ornithine, diaminobutyric acid, and/or homolysine.

The branched hydrophobic sequences (or tails) are preferably each from about 3 residues to about 11 residues in length, and more preferably from about 4 to about 10 residues in length, and even more preferably from about 5 to about 9 residues in length. In one or more embodiments, the hydrophobic tails are derived from sequence information for an internal fragment of the human di-hydropyridine-sensitive L-type calcium channel segment CaIVS3 (DPWNVFD-FLIVIGSIIDVILSE; SEQ ID NO: 2). In the CaIVS3 context, the peptide is part of a transmembrane helix that forms the central water-lined pore of a calcium channel. The hydrophobic segments of the peptide are synthetic versions of this sequence and are preferably selected from the group consisting of XLIVIGSII (SEQ ID NO: 3), XLIVI (SEQ ID NO: 4), and VFFIVIL (SEQ ID NO: 5), where X can be F, Y, W, or cyclohexylalanine. SEQ ID NO: 5 is a novel sequence loosely based on the CaIVS3 hydrophobic segment. In the new primary structural context all these branched sequences adopt a beta-sheet structure. In some embodiments, the N-terminal end of each hydrophobic tail can be capped with an acetyl group, —NH$_2$, naphthalene, fluorenylmethyloxycarbonyl, and/or anthracene.

It is particularly preferred that the peptides used to form the coating are selected from the group consisting of bis(h)-K—K$_n$, where h is a hydrophobic amino acid sequence selected from the group consisting of XLIVIGSII ("h$_9$"; SEQ ID NO: 3), XLIVI ("h$_5$"; SEQ ID NO: 4), and VFFIVIL (SEQ ID NO: 5), where X can be F, Y, W, or cyclohexylalanine; —K— is a branched lysine residue, K is a hydrophilic lysine residue, and n is from about 1 to about 7 (preferably from about 1 to about 6, and more preferably from about 1 to about 5). As noted above, the N-terminal end of each h sequence can be capped with an acetyl group (Ac), —NH$_2$, naphthalene, fluorenylmethyloxycarbonyl, and/or anthracene. Likewise, —K— can be replaced with diaminopropionic acid, ornithine, diaminobutyric acid, and/or homolysine.

The peptides preferably have a molecular weight ranging from about 781 Da to about 3345 Da, and more preferably from about 1116 Da to about 2999 Da, and even more preferably from about 1675 Da to about 2653 Da. The "molecular weight" for these peptides is an average weight calculated based upon the total MW of the actual amino acids present divided by the # of residues. The peptides preferably have an overall chain length ranging from about 7 amino acid residues to about 29 amino acid residues, more preferably from about 10 residues to about 26 residues, and even more preferably from about 15 residues to about 23 residues. Particularly preferred peptides are selected from the group consisting of bis(h$_9$)-K—K$_4$, bis(h$_5$)-K—K$_4$, and N-acetylated derivatives thereof.

In one or more embodiments, functional groups and/or various moieties can be attached to the C-terminal lysyl epsilon amino head group or the C-terminal carboxyl group. The term "functional moiety" is used herein to encompass functional groups, targeting moieties, and active agents that may be attached to the outer surface of the peptide layer. Exemplary functional moieties that can be attached include fluorophores, dyes, targeting moieties and ligands, antibodies, cysteine, cysteamine, biotin, biocytin, nucleic acids, polyethylene glycol (PEG), organometallic compounds, (e.g., methyl mercury), radioactive labels, —COOH, —CONH$_2$, —SH, and the like. Multiple such moieties can also be attached in a chain of sequential order from the C-terminal head group (amino or carboxyl group) using aliphatic spacers to separate different moieties. Thus, the invention provides the opportunity to create multi-functionalized nanoparticles. Since the individually modified peptides self-assemble to form the outer leaflet of the bilayer, any number of functional moieties can be adducted onto individual peptide sequences that comprise part of the assembled outer leaflet.

In one or more embodiments, the nanoparticle core is coated with a monolayer of peptides. In one or more embodiments, the peptide monolayer consists essentially (or even consists) of a single peptide type and/or two or more peptide types of the same chain length. The monolayer-coated nanoparticles are mono-dispersed with the hydrophobic tails of the amphipathic, branched peptides exposed to the solvent. The monolayer preferably coats substantially the entire surface of the nanoparticle, such that the nanoparticle core is completely encapsulated thereby. The number of peptides required to form a monolayer will be dependent upon the size of the nanoparticle and can be calculated using molecular modeling. In aqueous solution, the hydrophobic segments of the peptide associate generating nanoparticle aggregates. Over time, large monolayer-coated nanoparticle aggregates can be formed.

In one or more embodiments, the peptide coating is preferably characterized by a bilayer morphology. The bilayer structure is characterized by an inner leaflet (or monolayer) and an outer leaflet (or monolayer). The inner leaflet presents an inner surface facing the nanoparticle core, the outer leaflet presents an outer surface facing the environment, where the bilayer comprises a hydrophobic central region between the inner and outer surfaces. The inner and outer surfaces are characterized by hydrophilic head group regions of the peptides, while the hydrophobic central region is characterized by the interacting hydrophobic tail regions of the peptides. More preferably, the peptide coating consists (or consists essentially) of a bilayer of peptides associating through hydrogen bonding, hydrophobic interactions and Pi-Pi stacking of the aromatic residues. That is, the peptide coating, although having a morphology similar to a lipid bilayer, is preferably substantially free of lipids, phospholipids, or detergents. As used herein the term “substantially free” with respect to the bilayer means that such segments are not embedded in the bilayer structure, which is preferably comprised entirely of peptides. It will be appreciated that although certain compounds or segments are preferably excluded from being embedded in the bilayer, they may be tethered to the surface of the bilayer, and in particular extend from the outer surface of the bilayer coating.

In one or more embodiments, the bilayer is heterogeneous, comprising at least two different peptides, preferably having different chain lengths. More specifically, the inner leaflet of the bilayer comprises a plurality of a first amphipathic, branched peptide having a first number of amino acid residues, and the outer leaflet comprises a plurality of a second amphipathic, branched peptide having a second number of amino acid residues, where the first number of amino acid residues is different from the second number of amino acid residues. In one or more embodiments, the nanoparticle peptide bilayer consists (or consists essentially) of alternating and interlocking sequences bis($h_9$)-K—$K_4$ and bis($h_5$)-K—$K_4$, or the N-acetylated derivatives thereof. More specifically, in some embodiments, the inner leaflet comprises (consists essentially or consists of) a plurality of bis($h_9$)-K—$K_4$ peptides, while the outer leaflet comprises (consists essentially or consists of) a plurality of bis($h_5$)-K—$K_4$ peptides.

In one or more embodiments, the bilayer is homogeneous, comprising a single peptide type, but nonetheless forming a bilayer. More specifically, the inner leaflet of the bilayer comprises a plurality of a first amphipathic, branched peptide having a first number of amino acid residues, and the outer leaflet comprises a plurality of a second amphipathic, branched peptide having a second number of amino acid residues, where the first number of amino acid residues is the same as the second number of amino acid residues. Thus, for example, in some embodiments, the inner leaflet comprises (consists essentially or consists of) a plurality of bis($h_9$)-K—$K_4$ peptides, while the outer leaflet comprises (consists essentially or consists of) a plurality of bis($h_9$)-K—$K_4$ peptides. Likewise, the inner leaflet may comprise (consists essentially or consists of) a plurality of bis($h_5$)-K—$K_4$ peptides, while the outer leaflet comprises (consists essentially or consists of) a plurality of bis($h_5$)-K—$K_4$ peptides.

This homogenous bilayer is formed using the same procedures described for the heterogeneous bilayer, except that the same peptide is again added to the monolayer peptide-adducted nanoparticles, instead of adding a different type of peptide. Since the peptides are amphipathic, the same peptide type will nonetheless interact to create a similar bilayer morphology, as seen when using two different peptides according to the invention.

In the bilayer morphology, the peptides interact to form a beta sheet structure in the hydrophobic central region. The term “beta-sheet” conformation or structure, as used herein, refers to secondary protein structure where the protein forms overlapping layers, thus forming a beta-pleated sheet. Such beta-pleated sheets in the invention reside in a “parallel orientation” (i.e., the N-termini of successive strands are oriented in the same direction).

Methods of forming the nanoparticulates are also described herein. The method involves first tethering one of the peptides to a nanoparticle core in solution, followed by assembling the bilayer by adding the other peptide under appropriate conditions. It will be appreciated that having mono-disperse bilayer coated nanoparticles is an entirely new concept.

The two peptide layers are added sequentially. With reference to FIG. 2, initially a peptide monolayer is formed using thiol chemistry in toluene after pretreating the peptides with dilute ammonium hydroxide. The peptide is fully soluble in toluene after this treatment. In one or more embodiments, the peptide used for the initial conjugation is bis($h_9$)-K—$K_4$, which is first N-acetylated and modified with a cysteine residue: $(Ac\text{-}h_9)_2$-K—$K_4$-Cys-$CONH_2$, although it will be appreciated that any of the peptide variations discussed above could be used. Once coupled, the pH is lowered to pH 7. These peptide monolayer coated nanoparticles are now miscible in 50% trifluoroethanol (TFE). The peptide monolayer coated nanoparticles are suspended in 50% TFE, and then mixed with an excess of a second branched peptide. In one or more embodiments, the second peptide used is bis($h_5$)-K—$K_4$, which has been N-acetylated: $(Ac\text{-}h_5)_2$-K—$K_4$—$CONH_2$, although it will be appreciated that any of the peptide variations discussed above could be used. It is particularly preferred that this second peptide further include functional groups or targeting moieties attached near the C-terminal position. See FIG. 3. Upon mixing with the second peptide a bilayer spontaneously forms producing mono-dispersed bilayer coated nanoparticles. The resulting bilayer-coated nanoparticles are now miscible in water. The resulting nanoparticulates can be stored indefinitely in either a sterile aqueous solution, dried, and/or lyophilized.

Pre-functionalizing the peptides, and particularly the second peptide, will allow for the incorporation of various cellular targeting molecules at defined stoichiometries on the aqueous exposed surface of the assembled bilayer coated nanoparticles, thus making for a versatile and biocompatible nano-delivery system.

In addition to the peptide variants above, the bilayer coating can be created using peptide-like molecules called peptoids. Peptoids are region-isomers of the described peptides generated by moving the side chain connectivity to the backbone by one atom; from C-alpha to the amide nitrogen, thus making peptoids repeating unit oligomers of N-substituted glycine. Due to the loss of chiral center (C-alpha) as well as hydrogen bond donor (NH) peptoids are more flexible than peptides as a consequence of the tertiary backbone amides being able to easily adopt both cis and trans conformations. Having the side chain functionality on the amide nitrogen also affords peptoids protection against proteases.

In one or more embodiments, the resulting nanoparticulates have a maximum surface-to-surface dimension of less than about 10 nm. This size difference will greatly influence cell uptake, biodistribution and clearance. In work described herein, 5-nm peptide-gold nanoparticles are readily taken up by HeLa cells in culture, with no apparent toxicity.

Another important aspect of the design of the nanoparticulates is the cationic nature of the solvent-exposed surface of the bilayer. This property makes them readily taken up by cells, helps them escape the endosome transport pathway as well as provides an ideal surface for negatively charged DNA to bind to through electrostatic forces. In one or more embodiments, the nanoparticulates can be used to deliver nucleic acids (e.g., DNA) to cells in culture. In one or more embodiments, the nucleic acid polymers are added to dried nanoparticulates in sterile water and added almost immediately to cells in culture using serum-free medium. After incubating for several hours (e.g., about four hours) at elevated temperatures (e.g., about 30-37° C.), any excess nanoparticulates are washed off and the cells placed in their preferred media. Transfection efficiency is typically measured after about 48 hours. The smaller size of the nanoparticulates may increase transfection efficiencies. Since the nanoparticulates are so small the double stranded DNA used in the experiments may recruit multiple particles to make DNA/nanoparticulate complexes. Anyone delivering DNA or RNA to cells would find this method attractive to use since it does not require any preconditioning of the cells prior to transfecting them and the cells take-up the particles with particles in normal media without any added agents or physical stimulation. The nanoparticulates have oligo lysine segments that are reminiscent of a known nuclear localization signal. We hypothesize that many of the nanoparticulates taken up by cells will translocate to areas adjacent to the the nucleus. Surface bound moieties dissociate and can then enter the nucleus. Once inside under the appropriate conditions they can cause DNA damage and apoptosis. If cancer-targeting signals are included on the surface of the nanoparticulates such damage can be reduced in normal cells and enhanced in cancer cells.

Advantageously, the coated nanoparticles can be prepared for targeting of specific cell surface receptors through adduction of the C-terminal lysine with different molecules or functional groups (functional moieties), such as cholesterol, mannose, TAT peptide, insulin, biotin, nucleotides, or any other suitable known surface targeting molecules, active/therapeutic agents, and combinations thereof. The targeting moieties can be conjugated to the peptide coating exterior surface (prior to or after nanoparticulate formation) and will therefore localize in and be selectively taken up by specific cells or tissues of a patient. Thus, the nanoparticles can be used for targeted therapies (e.g., gene therapy, cancer treatment, etc.), and nanodrug delivery by administering the nanoparticles having the targeting moieties to a patient. The targeting moiety is attached to the hydrophilic segments of the peptides. More preferably, the targeting moiety is attached to the hydrophilic segment of the second of the two peptides, which will occupy the outer layer of the bilayer membrane, thus presenting the targeting moiety on the exterior surface of the peptide coating after formation. The moiety will be recognized by the targeted region or tissue in the patient, and the nanoparticle will automatically localize in that region or tissue.

The nanoparticulates can be used in pharmaceutically-acceptable compositions for delivering the nanoparticles and/or functional groups and can be administered orally, intravenously, subcutaneously, intramuscularly, nasally, intraocularly, or aerosolized to a patient. In one or more embodiments, the composition is orally active. In one or more embodiments, the composition comprises the nanoparticulates dispersed in an oil coating. Advantageously, the peptide bilayer is resistant to high temperatures, chaotropes, and nucleases.

In one or more embodiments, the composition comprises a therapeutically-effective amount of nanoparticulates dispersed in a pharmaceutically-acceptable carrier or excipient. As used herein, a "therapeutically effective" amount refers to the amount of the supramolecular assemblies that will elicit the biological or medical response of a tissue, system, animal, or human that is being sought by a researcher or clinician, and in particular elicit some desired therapeutic effect. For example, in one or more embodiments, a therapeutically effective amount of the supramolecular assemblies is an amount that releases sufficient active agents to damage, kill, or otherwise destroy the cancerous tissue. One of skill in the art recognizes that an amount may be considered therapeutically effective even if the condition is not totally eradicated but improved partially. As used herein, the term "pharmaceutically-acceptable" means not biologically or otherwise undesirable, in that it can be administered to a subject, cells, or tissue, without excessive toxicity, irritation, or allergic response, and does not cause any undesirable biological effects or interact in a deleterious manner with any of the other segments of the composition in which it is contained. A pharmaceutically-acceptable carrier or excipient would naturally be selected to minimize any degradation of the nanoparticulates, functional groups, or attached active gents, and to minimize any adverse side effects in the subject, cells, or tissue, as would be well known to one of skill in the art. Pharmaceutically-acceptable ingredients include those acceptable for veterinary use as well as human pharmaceutical use. Exemplary carriers and excipients include aqueous solutions such as normal (n.) saline (~0.9% NaCl), phosphate buffered saline (PBS), and/or sterile water (DAW), oil-in-water or water-in-oil emulsions, and the like.

Also described herein is a method of targeting delivery of an active agent to a region of a patient comprising administering to a patient a nanoparticulate as described herein, which comprises a targeting moiety on the exterior surface of the bilayer coating. The moiety will be recognized by the targeted region or tissue in the patient, and the nanoparticulates will automatically localize in that region or tissue. The nanoparticulates can be injected directly into the target tissue, or can be administered systemically.

The approach described herein can also be used to create peptide coatings on metallic wires, such as nanowires. The term "nanowire" as used herein refers to wires with a nanometer-sized cross-sectional dimension (e.g., diameter or thickness), and particularly dimensions of less than 100 nm. Thus, the inventive process can be used as described herein, except that the metallic nanoparticle core is replaced with a metallic nanowire, and particularly a gold, silver, or copper nanowire. Peptide monolayers and bilayers can be formed adjacent the nanowire's surface, just as described for the nanoparticles.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding segments A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Introduction

Figure 4:
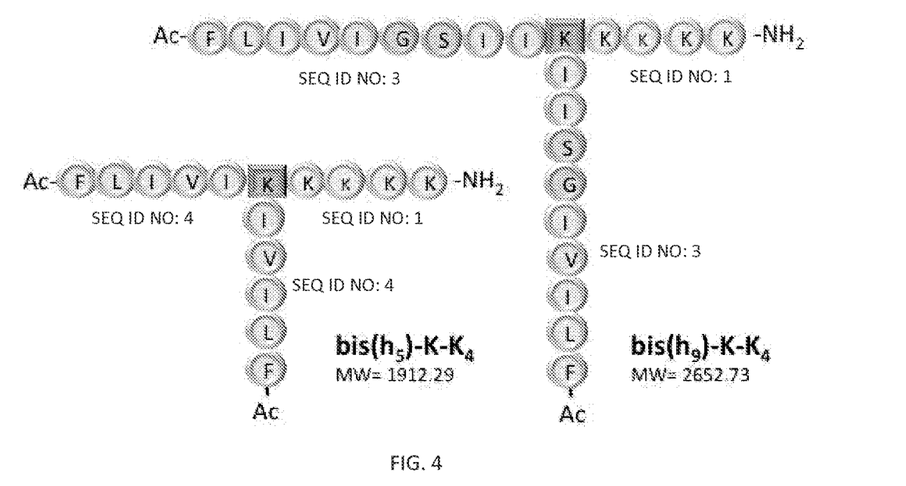
FIG. 4 sequences shows the sequences synthesized for use in the working examples.

In previous studies we have demonstrated that the branched amphiphilic peptides (BAPs)-bis ($h_5$)-K—$K_4$ and bis($h_9$)-K—$K_4$ (FIG. 4) spontaneously co-assemble at room temperature to form bilayer delimited poly-cationic capsules (BAPCs) or vesicles. Here the small letter h refers to the predominantly hydrophobic 5 or 9 residue segments: FLIVI (SEQ ID NO: 4) or FLIVIGSII (SEQ ID NO:3). The BAPCs are readily taken up by cultured cells through the endocytic pathway, escape the late endosomes and ultimately accumulate in the perinuclear region, persisting there without apparent degradation. To date we have entrapped small proteins and solutes as well as stably encapsulated alpha particle emitting radionuclides within the BAPCs. In the present study, we have developed a method of coating the surface of 5 nm gold nanoparticles with a branched peptide monolayer using thiol chemistry in toluene after pretreating the peptides with dilute ammonium hydroxide. When monolayer adducted gold nanoparticles are hydrated in the presence of excess BAPs, mono-dispersed gold nanoparticles are produced. If hydrated in the absence of additional peptide, bilayer separated gold nanoparticle aggregates were produced. Rhodamine labeled bilayer delimited 5 nm peptide-gold nanoparticles were readily taken up by HeLa cells in culture, with no apparent toxicity. Pre-functionalizing these peptides will allow for the incorporation of various cellular targeting molecules at defined stoichiometries on the aqueous exposed surface of the assembled bilayer coated gold nanoparticles, thus making for a versatile and biocompatible nano-delivery system.

Our approach builds on thiol-gold bonding chemistries using C-terminal cysteine adducted, self-assembling branched amphipathic peptides. These C-terminal cysteine incorporating peptides were originally developed to allow for the attachment of methyl mercury for transmission electron microscope imaging of peptide capsules which are composed of the two branched peptides. (Gudlur, S., Sukthankar, P., Gao, J., Avila, L. A., Hiromasa, Y., Chen, J., Iwamoto, T. and Tomich, J. M. (2012) Peptide nanovesicles formed by the self-assembly of branched amphiphilic peptides. PLoS One. 7, e45374.) Homo- and hetero-bilayers comprised of these two sequences will work in the present study, while this is not true for the 20-30 nm hollow capsules where the hetero assembly is required. In the previous work, the peptides are mixed under conditions where they are monomeric and dried, which after rehydration form bilayer delimited hollow spheres that share many properties with lipid vesicles including the trapping of solutes during capsule formation. (Sukthankar, P., Gudlur, S., Avila, L. A., Whitaker, S. K., Katz, B. B., Hiromasa, Y., Gao, J., Thapa, P., Moore, D., Iwamoto, T., Chen, J. and Tomich, J. M. (2013) Branched Oligopeptides Form Nanocapsules with Lipid Vesicle Characteristics. Langmuir 29: 14648-14654.) The capsules are considerably more robust than lipid vesicles and can withstand high temperatures and the recoil of encapsulated alpha-emitting radionuclides. (Sukthankar, P., Avila, L. A., Whitaker, S. K., Iwamoto, T., Morgenstern, A., Apostolidis, C., Liu, K., Hanzlik, R. P. Dadachova, E., Tomich, J. M. (2014). Branched Amphiphilic Peptide Capsules: Cellular Uptake and Retention of Encapsulated Solutes. Biochim. Biophys. Acta, Biomembranes 1838: 2296-2305.)

Materials and Methods

In this work, we first deprotonated the peptide bis($h_9$)-K—$K_4$-Cysteine by dissolving it in water and then adjusting the pH to 14.0 with ammonium hydroxide, incubating for 1 hr, and then drying the charge neutralized precipitate in vacuo. The peptide was then fully dispersed in toluene and mixed with the Dodecanethiol coated gold nanoparticles prepared using the Didodecyl-dimethylammonium bromide (DDAB)/water/toluene inverse micelle system. (Lin, X. M., Sorensen, C. M. and Klabunde, K. J. (2000) Digestive Ripening, Nanophase Segregation and Superlattice Formation in Gold Nanocrystal Colloids. J. Nanoparticle Res. 2: 157-164.) Thereafter, the Dodecanethiol was displaced with bis($h_9$)-K—$K_4$-Cys using a 200-fold excess of peptide by refluxing in toluene under argon for 90 min. After drying in vacuo, the resulting sample was suspended in 1:1 Trifluoroethanol (TFE):$H_2O$ and centrifuged to remove the insoluble unreacted product; excess free peptide was removed by filtering the suspension through a 30 kDa MWCO filter.

Figure 5:
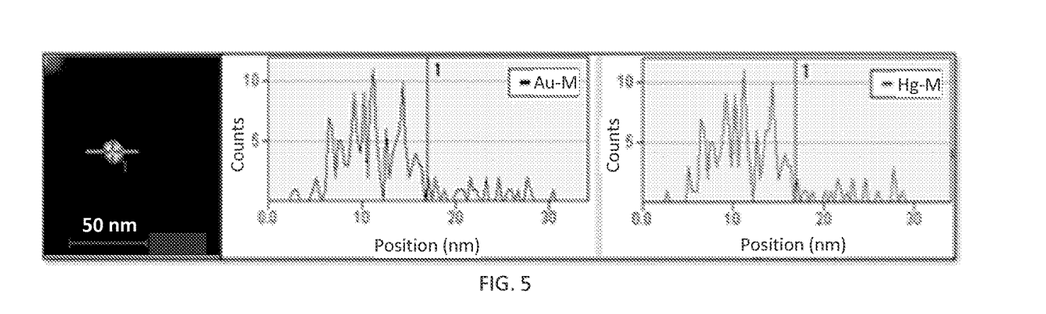
FIG. 5 shows the energy dispersive X-ray (EDX) spectra for the M shells of co-localized gold and mercury in PB-GNPs. The left panel shows the 10 nm Hg-labeled peptide bilayer Au particle that was scanned. The center panel shows the spectra counts recorded while scanning the surface for gold while the right panel shows the spectral counts observed for mercury contained in the outer leaflet comprised solely of the methyl mercury adducted bis($h_5$)-K—K4-Cys peptide.

For the scanning transmission electron microscopy studies, we included 30 mol % of bis($h_5$)-K—$K_4$-Cys-Hg—$CH_3^2$ in the outer leaflet. Energy dispersive X-ray (EDX) analysis on a scanned single 10 nm PB-GNPs showed overlapping signals for the gold and the bound mercury containing peptide coating, confirming its addition as the outer leaflet (FIG. 5).

Figure 6:
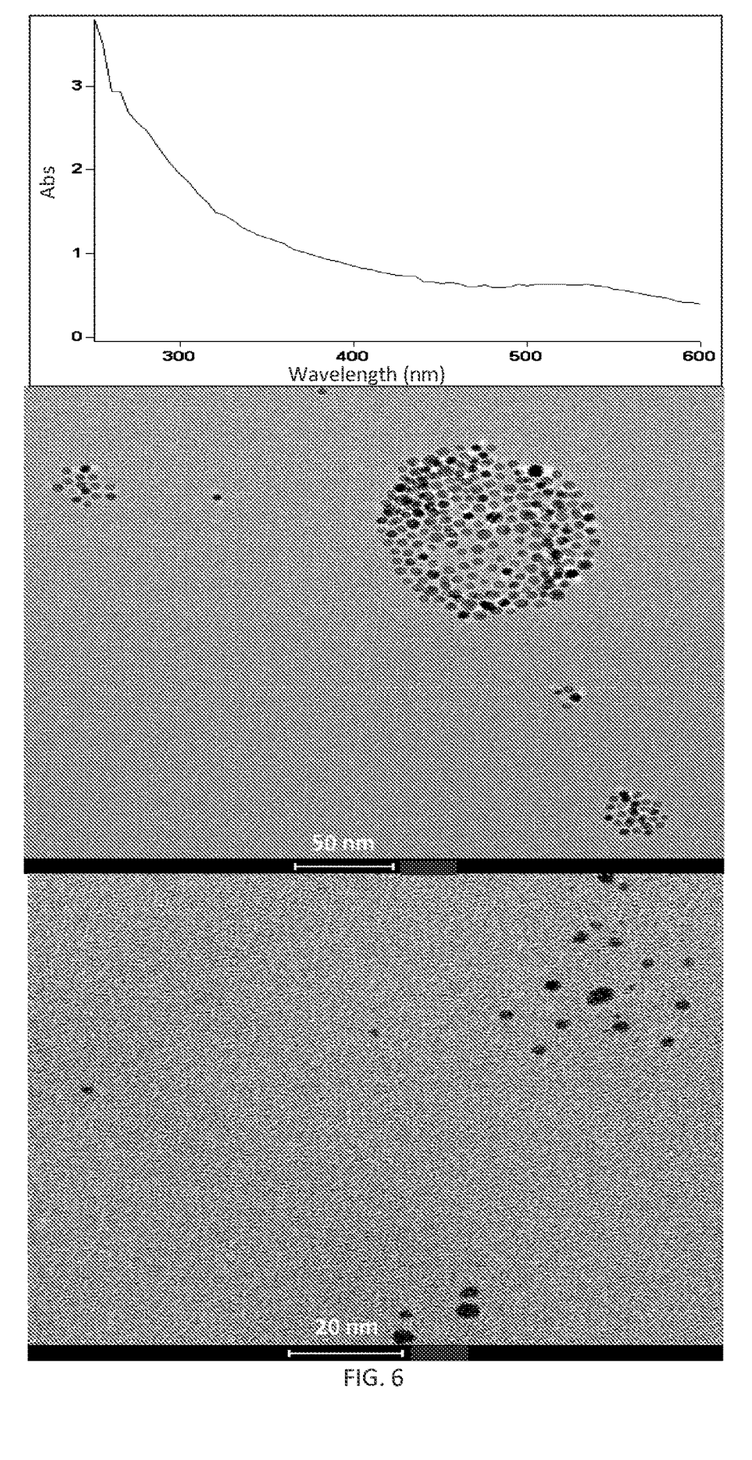
FIG. 6 shows the characterization of peptide-coated GNPs. Top panel: UV/Vis spectra of the bis($h_9$)-K—$K_4$-Cys-GNPs. Middle panel: TEM image of the complexes formed by the bis($h_9$)-K—$K_4$-Cys-GNPs in H2O. Bottom panel: TEM image of mono-dispersed PB-GNPs in water.

The UV-Vis spectrum was recorded to verify adduction of peptide with the GNPs by detecting both the gold plasmon absorbance at 540 nm and the Phe absorbance at 257.5 nm (FIG. 6, top panel). This protocol yields GNPs coated with a monolayer of peptide. In 1:1 TFE:$H_2O$, the peptide adducted GNPs are mono dispersed with the hydrophobic tails of the peptides solvent-exposed. This colloidal suspension in a sealed container has proven to be stably maintained for at least six months.

At this point, the GNPs can be made mono-dispersed. In FIG. 6 (middle panel) the peptide adducted GNPs were placed on a negatively glow discharged copper TEM grid in 1:1 TFE:H₂O and allowed to dry. The increase in the H₂O concentration due to the TFE evaporation results in association of the hydrophobic segments of the bis(h₉)-K—K₄-Cys generating the types of aggregates shown. Because evaporation occurred rapidly, random distributions were trapped. Had the increase in water content occurred in solution over a longer time period, large complexes would be expected to form.

Water-soluble mono-dispersed peptide bilayer-gold nanoparticles (PB-GNPs) were generated by adding a 1.1:1 excess bis(h₅)-K—K₄ dissolved in 1:1 TFE: H₂O to bis(h₉)-K—K₄-Cys-adducted GNPs dispersed in 1:1 TFE: H₂O. Immediately after mixing, the solution was dried. Since the bis(h₅)-K—K₄ peptides are unable to form self-assembling capsules they can only complex with the hydrophobic tails of the bis(h₉)-K—K₄-cysteine peptide conjugated to the GNPs. Upon rehydration under mild acidic conditions a bilayer is formed that presents the oligo lysine portion of the bis(h₅)-K—K₄ peptides toward solvent (FIG. 6, bottom panel). This preparation was stable and used experimentally for over three months. While most PB-GNPs were 5 nm in diameter a few 10 nm particles were observed (see FIG. 6, bottom panel). The larger size was analyzed to provide a better signal to noise ratio.

Figure 7:
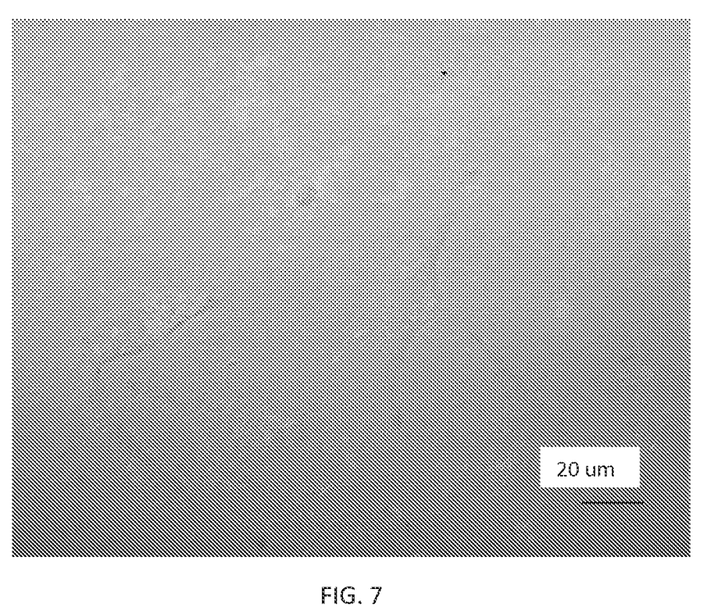
FIG. 7 shows the merged bright field and fluorescence confocal images of HeLa cells incubated with dye PB-GNPs after 4 h of incubation demonstrating cellular uptake of BP-GNPs in the examples.

Based on our earlier work with hollow bilayer delimited poly-cationic capsules (BAPCs) showing solutes encapsulation and cellular uptake, soluble mono-dispersed peptide bilayer coated GNPs were prepared containing 30 mol % bis(h₅)-K—K₄-Carboxytetramethylrhodamine. The dye was conjugated to the C-terminal lysine ε-amino group during synthesis. The dye-labeled BP-GNPs were added to Hela cells in Opti-MEM® (Life Technologies, Grand Island, N.Y.) and incubated for 4 hr at 37° C. Subsequently the cells were washed twice with Dulbecco's phosphate-buffered saline and the media was replaced. The cells were analyzed 30 min later using confocal microscopy (FIG. 7). In the figure, numerous washed Rhodamine B labeled PB-GNPs appear to be both inside the cell as well as bound to the surface. The treated cells were maintained in culture for two weeks through two trypsinizations followed by reseeding before imaging them on the confocal microscope. By this time only a few dye-coated GNPs were visible. The cells remained viable throughout the experiment suggesting that the coated GNPs were well tolerated but cleared. In earlier experiments with dye-labeled BAPCs these capsules were easily detected after two weeks. The major difference between these two systems is the size of the colloids with the pure peptide BAPCs ranging from 20-30 nm in diameter versus the 5 nm diameter PB-GNPs.

Conclusions

Dodecanethiol-adducted gold nanoparticles in toluene were converted to bis(h₉)-K—K₄-Cys-GNPs by refluxing under argon. The peptide was fully soluble in toluene once the lysyl-residues were deprotonated at elevated pH. The replacement of the thiol alkane with peptide did not involve any color change. The mono-dispersed peptide adducted GNPs are fully suspended in 1:1 TFE:H₂O with the branched hydrophobic tails of the peptide solvent exposed. When the TFE concentration is reduced the peptide-GNPs begins to assemble through the association of the branched hydrophobic segments. These complexes are not water-soluble. If the mono dispersed peptide adducted GNPs suspended in 1:1 TFE:H₂O are exposed to excess free peptide, a bilayer structure forms around individual peptide coated GNP, keeping them mono-dispersed and fully suspended in water. Labeling the GNPs through the addition of methyl mercury or dye labeled bis(h₅)-K—K₄ peptide provides additional evidence for the formation of a peptide bilayer on the surface of the GNPs. By adding a second self-assembling layer, their amino functional groups on the GNPs, can be multi-fictionalized at precise stoichiometries with one or more labels or cell targeting ligands. These stable colloidal particles are water-miscible and are readily taken up, in vitro, by HeLa cells. These bio-compatible and tunable GNPs colloidal nanoparticles are one of the smallest constructs with potential use as an in vivo drug delivery vehicle.

What is claimed:

1. A nanoparticulate comprising:
   a metallic nanoparticle core; and
   a peptide bilayer coating encapsulating said nanoparticle core and being covalently bonded directly thereto, said bilayer coating comprising a plurality of branched, amphipathic peptides, each of said peptides comprising a C-terminal hydrophilic segment coupled to a branch point, said branch point being coupled to two respective N-terminal hydrophobic segments, wherein said bilayer coating comprises:
   an inner leaflet comprising a first plurality of said branched, amphipathic peptides, wherein said C-terminal hydrophilic segments of said first plurality of branched, amphipathic peptides are oriented toward and covalently bonded to said nanoparticle core; and
   an outer leaflet comprising a second plurality of said branched, amphipathic peptides, wherein said C-terminal hydrophilic segments of second plurality of branched, amphipathic peptides orient away from said nanoparticle core and define an outer surface of said peptide bilayer coating.

2. The nanoparticulate of claim 1, wherein said metallic nanoparticle is a gold nanoparticle, a silver nanoparticle, or a copper nanoparticle.

3. The nanoparticulate of claim 1, wherein said metallic nanoparticle core has a maximum surface-to-surface dimension of from about 1 nm to about 10 nm.

4. The nanoparticulate of claim 1, wherein said hydrophilic segment consists of from about 1 to about 7 lysine residues.

5. The nanoparticulate of claim 1, wherein said hydrophobic segments are selected from the group consisting of XLIVIGSII (SEQ ID NO: 3), XLIVI (SEQ ID NO: 4), and VFFIVIL (SEQ ID NO: 5), where X is F, Y, W, or cyclohexylalanine.

6. The nanoparticulate of claim 1, wherein said N-terminal hydrophobic segment is capped with an acetyl group, —NH$_2$, naphthalene, fluorenylmethyloxycarbonyl, or anthracene.

7. The nanoparticulate of claim 1, wherein said branch point is a branched lysine, diaminopropionic acid, ornithine, diaminobutyric acid, or homolysine.

8. The nanoparticulate of claim 1, said branched, amphipathic peptides being selected from the group consisting of bis(h)-K-$K_n$ and the N-acetylated derivatives thereof, where h is a hydrophobic amino acid sequence selected from the group consisting of XLIVIGSII (SEQ ID NO: 3), XLIVI (SEQ ID NO: 4), and VFFIVIL (SEQ ID NO: 5), where X is F, —K— is a branched lysine residue, K is lysine, and n is from about 1 to about 7.

9. The nanoparticulate of claim 1, said inner leaflet presenting an inner surface facing said nanoparticle core and said outer leaflet presenting said outer surface, wherein said bilayer coating comprises a hydrophobic central region between said inner and outer surfaces.

10. The nanoparticulate of claim 1, said first plurality of amphipathic, branched peptides having a first number of amino acid residues, and said second plurality of amphipathic, branched peptides having a second number of amino acid residues, wherein said first number of amino acid residues are the same or different from said second number of amino acid residues.

11. The nanoparticulate of claim 9, wherein each of said hydrophobic segments of said first and second plurality of peptides are oriented inward away from said inner and outer surfaces and defining said hydrophobic central region of said bilayer member.

12. The nanoparticulate of claim 11, said hydrophobic central region comprising interlocking hydrophobic segments wherein the hydrophobic segments of said first plurality of peptides interdigitate with the hydrophobic segments of said second plurality of peptides in a parallel beta-sheet structure.

13. The nanoparticulate of claim 1, wherein said bilayer is substantially free of lipids or phospholipids.

14. The nanoparticulate of claim 1, said bilayer being heterogeneous.

15. The nanoparticulate of claim 1, said bilayer being homogenous.

16. The nanoparticulate of claim 1, wherein said first plurality of amphipathic, branched peptides are bis(h9)-K-$K_4$ peptides, where h9 is FLIVIGSII (SEQ ID NO: 3), and said second plurality of amphipathic, branched peptides are bis(h5)-K-K4 peptides, where h5 is FLIVI (SEQ ID NO: 4).

17. The nanoparticulate of claim 1, wherein said nanoparticulate has a maximum surface-to-surface dimension of less than about 10 nm.

18. The nanoparticulate of claim 1, further comprising a functional moiety attached to said outer surface via a C-terminal hydrophilic segment of said second plurality of amphipathic, branched peptides.

19. The nanoparticulate of claim 18, wherein said functional moiety is selected from the group consisting of fluorophores, dyes, targeting moieties and ligands, cysteine, cysteamine, biotin, biocytin, nucleic acids, polyethylene glycol, organometallic compounds, radioactive labels, —COOH, —CONH2, —SH, and sequentially linked combinations thereof.

20. The nanoparticulate of claim 18, comprising at least two functional moieties separated using aliphatic spacers.

21. The nanoparticulate of claim 18, wherein said functional moieties extend from the surface of said coating.

22. A composition comprising a plurality of nanoparticulates according to claim 1 dispersed in a pharmaceutically-acceptable carrier or excipient.

23. The nanoparticulate of claim 1, wherein said hydrophilic segment of said first plurality of branched, amphipathic peptides comprises a C-terminal cysteine residue covalently bonded to said nanoparticle core.

24. A method of targeting delivery of an active agent to a region of a patient comprising administering to a patient a plurality of nanoparticulates according to claim 1, wherein said nanoparticulates each further comprises at least one functional moiety extending from the surface of the peptide coating.

25. A method of transfecting a cell, comprising incubating cells with a nanoparticulate according to claim 1, said nanoparticulate further comprising nucleic acid bound to the surface of said coating.

\* \* \* \* \*

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic lysine residue C-terminal segment

<400> SEQUENCE: 1

Lys Lys Lys Lys
1

<210> SEQ ID NO 2
<211> LENGTH: 22
<212> TYPE: PRT
<213> ORGANISM: Homo sapiens

<400> SEQUENCE: 2

Asp Pro Trp Asn Val Phe Asp Phe Leu Ile Val Ile Gly Ser Ile Ile
1               5                   10                  15

Asp Val Ile Leu Ser Glu
            20
```

```
<210> SEQ ID NO 3
<211> LENGTH: 9
<212> TYPE: PRT
<213> ORGANISM: Artificial Sequence
<220> FEATURE:
<223> OTHER INFORMATION: Synthetic sequence designed from internal
      fragment of human dihydropyridine sensitive L-type calcium channel
      segment CaIVS3
<220> FEATURE:
<221> NAME/KEY: MISC_FEATURE
<222> LOCATION: (1)..(1)
<223> OTHER INFORMATION: Xaa is F, Y, W, or cyclohexylalanine

<400> SEQUENCE: 3

Xaa Leu Ile Val Ile Gly Ser Ile Ile
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic sequence designed from internal
      fragment of human dihydropyridine sensitive L-type calcium channel
      segment CaIVS3
<220> FEATURE:
<221> NAME/KEY: MISC_FEATURE
<222> LOCATION: (1)..(1)
<223> OTHER INFORMATION: Xaa is F, Y, W, or cyclohexylalanine

<400> SEQUENCE: 4

Xaa Leu Ile Val Ile
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic sequence designed from internal
      fragment of human dihydropyridine sensitive CaIVS3 hydrophobic
      segment

<400> SEQUENCE: 5

Val Phe Phe Ile Val Ile Leu
1               5
```